United States Patent [19]

Yamazaki et al.

[11] Patent Number: 4,590,281
[45] Date of Patent: May 20, 1986

[54] PROCESS FOR PREPARING ALDEHYDES

[75] Inventors: Yasuo Yamazaki, Machida; Takehiko Suzuki, Tokyo, both of Japan

[73] Assignee: Nippon Petrochemicals Company, Tokyo, Japan

[21] Appl. No.: 587,166

[22] Filed: Mar. 7, 1984

[30] Foreign Application Priority Data

Mar. 9, 1983 [JP] Japan ................... 57-37314

[51] Int. Cl.$^4$ ............... C07C 25/125; C07C 45/30
[52] U.S. Cl. ........................ 548/545; 570/182; 568/436; 568/437; 564/155; 564/218
[58] Field of Search ............ 568/437, 436; 564/218, 564/155; 570/182; 548/545

[56] References Cited

U.S. PATENT DOCUMENTS

| | | | |
|---|---|---|---|
| 2,878,293 | 3/1959 | Kinzer | 570/182 |
| 3,862,333 | 1/1975 | Chalupa et al. | 570/182 |
| 4,070,374 | 1/1978 | Chalk et al. | 568/437 |
| 4,087,554 | 5/1978 | Haydock et al. | 570/182 |
| 4,151,175 | 4/1979 | Crivello et al. | 570/182 |
| 4,238,394 | 12/1980 | Crivello et al. | 570/182 |

OTHER PUBLICATIONS

Caserio et al., *J. Am. Chem. Soc.*, vol. 81, pp. 336–342, (1959).
Crivello et al., *Chemical Abstracts*, vol. 90, #203621j, (1979).
Cookson et al., *Chemical Abstracts*, vol. 91, #174950d, (1979).

*Primary Examiner*—Natalie Trousof
*Assistant Examiner*—Bruce D. Gray
*Attorney, Agent, or Firm*—Scully, Scott, Murphy & Presser

[57] ABSTRACT

Provided is a process for preparing an aldehyde or aldehydes represented by the following formula (III), characterized in that a diaryliodonium salt represented by the following formula (I) is reacted with an unsaturated alcohol represented by the following formula (II) in a solvent containing a base in the presence of a transition metal catalyst at a temperature in the range of room temperature to 100° C.:

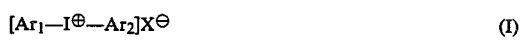

$$[Ar_1-I^{\oplus}-Ar_2]X^{\ominus} \quad (I)$$

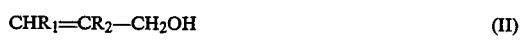

$$CHR_1=CR_2-CH_2OH \quad (II)$$

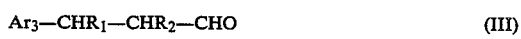

$$Ar_3-CHR_1-CHR_2-CHO \quad (III)$$

wherein $Ar_1$ and $Ar_2$, which may be alike or different, are each an aryl group which may have a substituent group or groups, $X^{\ominus}$ is a counter ion which is inert to the above reaction, $Ar_3$ is the same aryl group as $Ar_1$ or $Ar_2$, and $R_1$ and $R_2$ are each hydrogen atom or an alkyl group of $C_1$ to $C_{12}$.

10 Claims, No Drawings

PROCESS FOR PREPARING ALDEHYDES

BACKGROUND OF THE INVENTION

The present invention relates to a novel process for preparing aldehydes having aryl groups.

Aldehydes having aryl groups, for example, cyclamen aldehyde and lily aldehyde both used as perfumes in soaps, cosmetics, etc. have heretofore been prepared through a relatively large number of steps involving introduction of aldehyde group into cumene, t-butylbenzene, etc., an aldol condensation with propionaldehyde and subsequent hydrogenation.

OBJECT OF THE INVENTION

The object of the present invention is to provide a process for preparing aldehydes having aryl groups easily in a simple manner through a novel reaction.

SUMMARY OF THE INVENTION

The present invention resides in a process for preparing an aldehyde represented by the following formula (III), characterized in that an unsaturated alcohol represented by the following formula (II) is reacted with a diaryliodonium salt represented by the following formula (I) in a solvent containing a base in the presence of a transition metal catalyst:

$$[Ar_1-I^{\oplus}-Ar_2]X^{\ominus} \qquad (I)$$

$$CHR_1=CR_2-CH_2OH \qquad (II)$$

$$Ar_3-CHR_1-CHR_2-CHO \qquad (III)$$

wherein $Ar_1$ and $Ar_2$, which may be alike or different, are each an aryl group which may have a substituent group or groups, $X^{\oplus}$ is a counter ion which is inert to said reaction, $Ar_3$ is the same aryl group as $Ar_1$ or $Ar_2$, and $R_1$ and $R_2$ are each hydrogen or $C_1$–$C_{12}$ alkyl such as methyl, ethyl, heptyl.

DETAILED DESCRIPTION OF THE INVENTION

In the present invention, diaryliodonium salts of the foregoing general formula (I) wherein the aryl groups may have substituent groups are used as starting materials. Each aryl group is a monovalent substituent group derived by removing one hydrogen atom from the aromatic nucleus of a condensed or non-condensed type aromatic hydrocarbon which may have substituent groups. For example, it is derived from a non-condensed type aromatic hydrocarbon such as benzene or indane, a condensed type aromatic hydrocarbon such as naphthalene, or a substituted product thereof. The two aryl groups may be the same or different.

Preferred diaryliodonium salts are such diphenyliodonium salts as represented by the following formula:

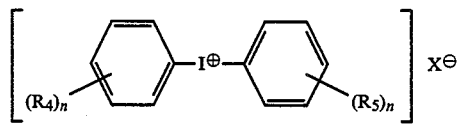

wherein n and m are each an integer of 0 to 3, and $R_4$ and $R_5$, which may be alike or different, are each hydrogen atom, $C_1$–$C_{12}$ alkyl or cycloalkyl groups, aryl groups, halogenoalkyl groups, halogen atom, alkoxy groups, nitro, and N-acylamino groups. Examples of aryl groups as $R_4$ or $R_5$ are phenyl, tolyl, xylyl and naphtyl. Examples of halogenoalkyl groups are chloromethyl and bromomethyl. Examples of alkoxy groups are methoxy, ethoxy and propoxy. Examples of N-acylamino groups are N-acylamino, N,N-diacetylamino and succinimido.

As examples of symmetric diaryliodonium, wherein the two aryl groups are the same, mention may be made of diphenyliodonium, ditolyliodonium, dicumenyliodonium, bis(alkylphenyl)iodoniums such as bis(isobutylphenyl)iodonium and bis(t-butylphenyl)iodonium, bis(cyclohexylphenyl)iodonium, dibiphenylyliodonium, bis(halogenoalkylphenyl)iodoniums such as bis(trifluoromethylphenyl)iodonium, bis(halogenophenyl)iodoniums such as bis(chlorophenyl)iodonium and bis(bromophenyl)iodonium, bis(carboxylphenyl)iodonium, bis(alkoxyphenyl)iodoniums such as bis(methoxyphenyl)iodonium and bis(ethoxyphenyl)iodonium, bis(nitrophenyl)iodonium, and bis(acylaminophenyl)iodoniums such as bis(acetylaminophenyl)iodonium.

There also may be used asymmetric type diaryliodonium salts wherein the two aryl groups are different, examples of which are salts of 4-tolylphenyliodonium, 4-t-butylphenylphenyliodonium, 4-methoxyphenylphenyliodonium, 3-chlorophenylphenyliodonium, 4-bromophenylphenyliodonium and 4-chlorophenyl-4'-tolyliodonium.

These diaryliodoniums form salts with the counter ion $X^{\oplus}$ as shown in the foregoing formulae (I) and (IV), but the counter ion $X^{\ominus}$ is not essential to the present invention; it may be any anion inert to the reaction. Examples of counter ions, which usually are selected according to methods of obtaining iodonium salts, include mineral acid anions such as bisulfate ion, chloride ion, bromide ion and iodide ion, and metal halide ions such as boron tetrafluoride ion, phosphorus hexafluoride ion, arsenic hexafluoride ion and antimony hexafluoride ion. These counter ions may be ion-exchanged with each other, if required. Bromide and other halide ions are particularly preferred.

Halogen salts of diaryliodoniums can be produced according to the method described in British Pat. Nos. 1,114,950; 1,542,068; and 1,572,620, or the Beringer et al's method described in *J. Am. Chem. Soc.* 81, 342 (1959). For example, they can be produced from alkylbenzenes such as benzene, toluene, iso-propylbenzene, iso-butylbenzene and t-butylbenzene, indane, halogenated benzenes such as chlorobenzene and bromobenzene, benzoic acid, anisole, nitrobenzene, acetanilide, and biphenyl. As an example, in the method of producing diphenyliodonium salt from benzene, benzene and potassium iodate ($KIO_3$) are added into acetic anhydride and mixed, then a mixed solution of acetic anhydride and concentrated sulfuric acid is dropwise added and stirred, thereafter an aqueous saturated ammonium chloride solution is added to allow precipitation to take place, followed by filtration and recrystallization, whereby diphenyliodonium chloride can be obtained, which may be further subjected to ion exchange of counter ion, if required.

Examples of the unsaturated alcohol of the foregoing formula (II) to be reacted with the diaryliodonium salt are allyl alcohol, methallyl alcohol, 2-ethyl-2-propen-1-ol, 2-heptyl-2-propen-1-ol and 2-buten-1-ol.

By reacting the diaryliodonium salt with the unsaturated alcohol in a solvent containing a base in the presence of a transition metal catalyst, there is obtained an aldehyde of the foregoing formula (III). This can be expressed by the following reaction formula:

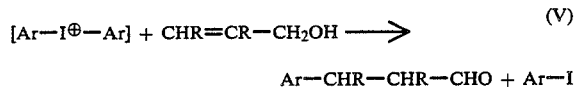
(V)

The aldehyde thus obtained is a 3-aryl-propanal or a substituted product thereof. The aryl group of the aldehyde corresponds to any of the aryl groups of the diaryliodonium slat. Therefore, if a diphenyliodonium salt of the foregoing formula (IV) is used as the starting diaryliodonium salt, there is obtained an aldehyde of the following formula (VI):

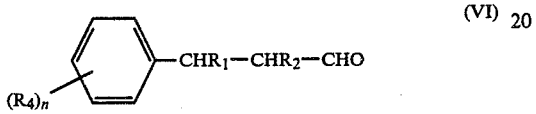
(VI)

wherein $R_4$ and n are as defined in the foregoing formula (IV) and $R_1$ and $R_2$ are as defined in the foregoing formula (II).

Therefore, by reacting bis(p-iso-propylphenyl)iodonium salt with methallyl alcohol there is produced cyclamen aldehyde[3-(p-iso-propylphenyl)-2-methylpropanal], and by reacting bis(p-t-butylphenyl)idonium salt with methallyl alcohol there is produced lily aldehyde[3-(p-t-butylphenyl)-2-methylpropanal].

The aldehydes thus obtained are each a single aldehyde because the starting diaryliodonium salts are symmetric type iodonium salts with two aryl groups being the same. On the other hand, in the case of using an asymmetric type diaryliodonium salt wherein the two aryl groups are different, as a starting material, there are produced two kinds of aldehydes. For example, if phenyl-4-iso-propylphenyliodonium salt is reacted with methallyl alcohol, there are produced 3-(p-isopropylphenyl)-2-methylpropanal and 3-phenyl-2-methylpropanal. Likewise, by reacting phenyl-4-t-butylphenyliodonium with methallyl alcohol, there are produced 3-p-t-butyl-2-methylpropanal and 3-phenyl-2-methylpropanal.

As the base used in the present invention, there may be used any base if only it dissolves in the solvent used, and activates the transition metal catalyst and does not suppress the reaction, that is, does not inactivate the catalyst by its coordinating to the transition metal. After the reaction, the base neutralizes with the counter ion of the iodonium salt. Examples of the base used in the invention are tertiary alkylamines such as triethylamine, tripropylamine, tributylamine, dimethylaniline and diethylaniline, alkali metal salts such as sodium and potassium salts of lower fatty acids, e.g. sodium acetate, potassium acetate, sodium formate and potassium formate, carbonates and bicarbonates of alkali metals, and basic oxides such as oxides of alkaline earth metals.

The base may be used in an amount sufficient to neutralize the counter ion of the diaryliodonium salt used. If its amount is smaller than a stoichiometric amount, the yield of the desired aldehyde will become lower. Thus, its amount can be selected appropriately.

As the solvent used in the invention, there may be used any inert solvent which dissolves the diaryliodonium salt even a little and which does not participate in the reaction. Examples are lower alcohols such as methanol and ethanol, ketones such as acetone and methyl ethyl ketone, ethers such as dimethoxyethane, tetrahydrofuran and dioxane, as well as various polar solvents such as dimethylformamide (DMF), dimethyl sulfoxide (DMSO) and acetonitrile. When the base used can serve also as the solvent, it is not necessary to specially use the solvent.

The transition metal catalyst used in the present invention comprises a metal selected from Group VIII in the Periodic Table, for example, palladium, rhodium, ruthenium, platinum, iridium, osmium, or nickel, with a palladium catalyst being particularly preferred. These transition metals may be used as catalysts in various forms regardless of their oxidation numbers or whether they are in the form of complexes or not. In the case of palladium, there may be used palladium black, palladium supported on alumina or active carbon, divalent palladium compounds such as palladium halides, e.g. palladium chloride, palladium oxides and palladium salts of lower fatty acids, e.g. palladium acetate, as well as complexes such as bis(dibenzylideneacetone)palladium, acetylacetonepalladium, tetrakis(triphenylphosphine)palladium, bis(triphenylphosphine)dichloropalladium, and bis(triphenylphosphine)phenylpalladium iodide. In the case of rhodium, there also may be used its carbonyl complex. Examples of nickel catalysts include nickel (II) chloride and bis(triphenylphosphine)nickel (II) chloride.

The amount of the transition metal catalyst used is in the range of 0.1 to 10 mol%, preferably 1 to 5 mol%, per mol of the iodonium salt.

The reaction proceeds gently and quickly, and the reaction pressure and temperature may be selected according to the starting materials used. Usually, atmospheric pressure suffices as the reaction pressure, it being not necessary to specially apply pressure. However, the pressure may be applied to prevent the evaporation or loss of the starting alcohol in case the boiling point of the alcohol is low. The reaction temperature may be in the range of room temperature to 100° C. Preferably, it is below the boiling point of the solvent used. Further, a reaction time in the range of 0.5 to 10 hours usually suffices.

If the reaction after completion is followed by a thorough washing with water, extraction with ether for isolation and subsequent distillation or recrystallization, there can be obtained the aldehyde of the object product of the present invention.

In the reaction there is by-produced an iodoaryl, e.g. iodobenzene, as shown in the foregoing reaction formula. Since iodine is expensive and hence iodobenzene is also expensive, the utilization of the by-produced iodoaryl must be considered in order to render the process of the present invention economical and less expensive. As one method for utilizing the by-produced iodoaryl, there may be obtained a diaryliodonium salt from the by-produced iodoaryl, for example, according to the foregoing Beringer et al's method or the method disclosed in the specification of Japanese Patent Application No. 37315/1983 filed by the present applicant. Thus, if a diaryliodonium salt is obtained from the by-produced iodoaryl, the expensive iodine, that is, the iodoaryl, is utilized in a recycled manner without being lost, and consequently the process of the present invention becomes more economical.

For utilizing the by-produced iodoaryl in such a recycled manner, it is not desirable in the process of the present invention to use such as excess base as largely exceeds an amount equivalent to the diaryliodonium salt used. If an excess base is present, the by-produced iodoaryl will further react with unsaturated alcohol, if any, resulting in that the iodine in the iodoaryl is converted to a neutral iodine salt whose conversion to diaryliodonium salt is not easy. In other words, for re-utilizing the by-produced iodoaryl, it is necessary that the process of the present invention be practiced under conditions under which the iodoaryl is produced in an amount equimolar to the converted diaryliodonium salt.

Therefore, in order to render the process of the present invention more economical by recycling or re-utilizing the by-produced iodoaryl, the base should be used in an amount not largely exceeding an amount equivalent to the diaryliodonium salt used, or the unsaturated alcohol should be used in an amount not exceeding an amount equimolar to the diaryliodonium salt used. Either of both of these conditions should be satisfied. More specifically, it is preferable that the amount of the base used be in the range of 0.8 to 1.2 mols per mol of the diaryliodonium salt, or that of the unsaturated alcohol used be in the range of 0.8 to 1.2 mols per mol of the diaryliodonium salt. Both of these conditions may be satisfied at a time. As another condition for re-utilizing the by-produced iodoaryl, the reaction temperature should be set at a relatively low level, for example, in the range of room temperature to 80° C. This is because the reaction of the by-produced iodoaryl does not proceed so much in such low temperature range.

The following examples are given to further illustrate the present invention.

EXAMPLE 1

Diaryliodonium bromides of the following formula were prepared according to the foregoing Beringer et al's method, as shown in Table 1 below:

TABLE 1

$$\left[ R-\underset{}{\bigcirc}-I^{\oplus}-\underset{}{\bigcirc}-R \right] Br^{\ominus}$$

| Iodonium Salt | Substituent R | Yield of Iodonium Salt (%) | Melting Point of Iodonium Salt (°C.) |
| --- | --- | --- | --- |
| B | H | 77 | 195–198 |
| C | $CH_3$ | 89 | 167–170 |
| D | iso-$C_3H_7$ | 85 | 171–173 |
| E | tert-$C_4H_9$ | 89 | 167–168 |

Solvents (100 ml each), bases (100 mmol each) and the diaryliodonium salts (100 mmol each) shown in Table 1 were charged into three-necked flasks. After a thorough purging with nitrogen gas, catalysts (5 mmol each) were added and the temperature was raised to a predetermined level (50° C.). Then, allylic alcohol (100 mmol) was added at a time and reaction was allowed to proceed for predetermined periods of time. Thereafter, the reaction products were purified by repeating water-washing and extraction with ether, then analyzed by gas chromatography and identified by infrared and NMR spectra, the results of which are as shown in Table 2.

In this Example and the following Example 2 there were by-produced the corresponding iodoaryls almost quantitatively.

TABLE 2

| Run No. | Diaryliodonium Salt | Alcohol[1] | Base | Catalyst | Solvent | Reaction Time (hr) | Aldehyde | Yield[2] (%) |
| --- | --- | --- | --- | --- | --- | --- | --- | --- |
| 1 | B | A | (n-BU)$_3$N | Pd black | acetone | 3 | 3-phenylpropanol | 82 |
| 2 | B | A | " | " | methanol | 1 | " | 79 |
| 3 | B | A | $CH_3COOK$ | " | acetone | 3 | " | 18 |
| 4 | B | A | " | " | methanol | 3 | " | 95 |
| 5 | B | A | " | $PdCl_2$ | " | 3 | " | 90 |
| 6 | B | A | " | Pd(OCc)$_2$ | " | 3 | " | 91 |
| 7 | B | A | " | Pd(dba)$_2$[3] | " | 3 | " | 88 |
| 8 | B | A | " | Rh(CO)$_2$Cl$_2$ | " | 3 | " | 7 |
| 9 | B | M | (n-Bu)$_3$N | Pd black | acetone | 3 | 2-methyl-3-phenylpropanal | 31 |
| 10 | B | M | $CH_3COOK$ | " | methanol | 1 | " | 135 |
| 11 | B | M | (n-Bu)$_3$N | Pd—carbon | " | 3 | " | 45 |
| 12 | B | M | $NaHCO_3$ | " | " | 3 | " | 68 |
| 13 | C | M | $CH_3COONa$ | " | " | 3 | 2-methyl-3-(p-tolyl)-propanal | 100 |
| 14 | D | M | $CH_3COONa$ | " | " | 2 | cyclamen aldehyde | 96 |
| 15 | E | M | $CH_3COONa$ | " | " | 1 | lily aldehyde | 88 |

[1]A: allyl alcohol M: methallyl alcohol
[2]Yield based on diaryliodonium salt
[3]Pd(dba)$_2$: bis(dibenzylideneacetone)palladium

EXAMPLE 2

Diaryliodonium bromides prepared according to the Beringer et al's method were reacted in the same way as in Example 1, the results of which are as set out in Table 3.

| Diaryliodonium | m.p. (°C.) |
| --- | --- |
| F: bis(p-chlorophenyl)iodonium bromide | 204–205 |
| G: bis(p-methoxyphenyl)iodonium bromide | 201–202 |
| H: bis(m-nitrophenyl)iodonium bromide | 174–176 |

TABLE 3

| Run No. | Iodonium Salt | Alcohol[1] | Base | Catalyst | Solvent | Reaction Time (hr) | Aldehyde | Yield[2] (%) |
| --- | --- | --- | --- | --- | --- | --- | --- | --- |
| 16 | F | M | $CH_3COONa$ | Pd—carbon | methanol | 3 | 2-methyl-3-(4-chlorophenyl)propanal | 98 |

TABLE 3-continued

| Run No. | Iodonium Salt | Alcohol[1] | Base | Catalyst | Solvent | Reaction Time (hr) | Aldehyde | Yield[2] (%) |
|---|---|---|---|---|---|---|---|---|
| 17 | G | M | " | PdCl$_2$ | acetone | 3 | 2-methyl-3-(4-methoxyphenyl)propanal | 80 |
| 18 | H | M | " | " | methanol | 3 | 2-methyl-3-(3-nitrophenyl(propanal | 75 |

[1]1M: methallyl alcohol
[2]Yield based on diaryliodonium salt

EXAMPLE 3

The following diaryliodonium salts and the unsaturated alcohols shown in Table 4 were reacted in the same way as in Example 1, provided that palladium chloride, sodium acetate and methanol were used as catalyst, base and solvent, respectively, and the reaction was carried out for 8 hours, the results of which are as shown in Table 4.

| Diaryliodonium Salts | m.p. (°C.) |
|---|---|
| bis(4-heptylphenyl)iodonium bromide | paste-like |
| 4-t-butylphenylphenyliodonium | |
| bis[4-(N,N—disuccinimido)phenyl]iodonium iodide | 184–185° C. |

TABLE 4

| Run No. | Diaryliodonium Salts | Unsaturated Alcohol | Aldehyde | Yield (%) |
|---|---|---|---|---|
| 19 | bis(4-heptylphenyl)iodonium | allyl alcohol | 3-(4-heptylphenyl)propanol | 95 |
| 20 | diphenyliodonium | 2-heptyl-1-propene-3-ol | 3-phenyl-2-heptylpropanal | 90 |
| 21 | bis[4-(N,N—succinimido)phenyl]-iodonium | methallyl alcohol | 3-[4-N,N—succinimido)-phenyl]-2-methyl-propanal | 92 |
| 22 | bis(chloromethylphenyl)-iodonium | methallyl alcohol | 3-(4-chloromethylphenyl)-2-methyl-propanal | 88 |
| 23 | 4-t-butylphenylphenyliodonium | allyl alcohol | 3-phenylpropanal (53%) 3-(4-t-butylphenyl)-propanol (47%) | 90 |

*Yield based on iodonium salt.

What is claimed is:

1. A process for preparing aldehydes of formula III and iodoaryl of formula IV, characterized in that a diaryliodonium salt represented by formula I is reacted with an unsaturated alcohol represented by formula II in an inert solvent containing a base in the presence of an effectively catalytic amount of a transition metal catalyst at a temperature in the range of about room temperature to about 100° C.:

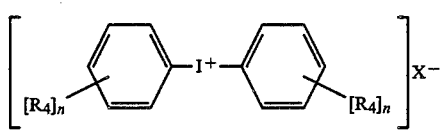

I $CHR_1=CR_2-CH_2OH$  II

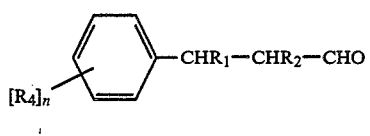

III

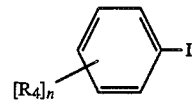

IV wherein
n is an integer of 0 to 3; each R$_4$, which may be alike or different, is hydrogen, halogen, C$_1$–C$_{12}$ alkyl, C$_3$–C$_{12}$ cycloalkyl, aryl, C$_1$–C$_{12}$ halogenoalkyl, C$_1$–C$_{12}$ alkoxy, nitro or C$_1$–C$_{12}$ N-acylamino groups;
X- is a counter ion which is inert to the above reaction; and
R$_1$ and R$_2$ are each hydrogen or C$_1$–C$_{12}$ alkyl.

2. The process of claim 1 wherein said formed iodoaryl is recycled to form additional diaryliodonium salt.

3. The process of claim 1 wherein said R$_4$ is methyl, isopropyl, tert-butyl, heptyl, chloro, methoxy, nitro, or N,N-succinimido.

4. The process of claim 1, wherein said transition metal catalyst is a palladium-based catalyst.

5. The process of claim 1, wherein said unsaturated alcohol is allyl alcohol or methallyl alcohol.

6. The process of claim 1, wherein said temperature is in the range of room temperature to 80° C.

7. The process of claim 1 wherein said base is present in an amount not substantially in excess of an equivalent amount of the diaryliodonium used.

8. The process of claim 1, wherein the amount of the said base is in the range of 0.8 to 1.2 moles per mole of said diaryliodonium salt.

9. The process of claim 1, wherein the unsaturated alcohol is present in an amount not substantially in excess of an equimolar amount of said diaryliodonium salt.

10. The process of claim 1, wherein the amount of the said unsaturated alcohol is in the range of 0.8 to 1.2 moles per mole of said diaryliodonium salt.

* * * * *